United States Patent [19]
Brichard et al.

[11] Patent Number: 5,854,203
[45] Date of Patent: Dec. 29, 1998

[54] TUMOR REJECTION ANTIGEN PRECURSOR PROCESSED TO AT LEAST ONE TUMOR REJECTION ANTIGEN PRESENTED BY HLA-A2

[75] Inventors: Vincent Brichard; Aline Van Pel, both of Brussels, Belgium; Catia Traversari, Milan, Italy; Thomas Wölfel, Mainz, Germany; Thierry Boon-Falleur; Etienne De Plaen, both of Brussels, Belgium

[73] Assignee: Ludwig Institute for Cancer Research, New York, N.Y.

[21] Appl. No.: 398,409

[22] Filed: Mar. 3, 1995

Related U.S. Application Data

[62] Division of Ser. No. 32,978, Mar. 18, 1993, Pat. No. 5,620,886.

[51] Int. Cl.⁶ .............................. A01N 37/18; C07K 1/00; C07H 21/02; G01N 33/574
[52] U.S. Cl. .............................. 514/2; 530/350; 536/23.1; 536/23.5; 435/172.1; 435/69.1; 435/252.3; 435/320.1; 435/7.23
[58] Field of Search .................................. 435/172.1, 69.1, 435/320.1, 252.3, 6, 7.23; 530/350; 536/23.1, 24.31, 24.33; 514/2

[56] References Cited

U.S. PATENT DOCUMENTS 5,487,974  1/1996  Boon-Falleur et al. .................. 435/6

OTHER PUBLICATIONS

Barinaga, *Science,* 257:880 (1992).

Fremont et al., *Science,* 257:919 (1992).

Matsumura et al., *Science,* 257:927 (1992).

Latron et al., *Science,* 257:964 (1992).

Traversari et al., *Immunogenetics,* 35:145 (1992).

van der Bruggen et al., *Science,* 254:1643 (1991).

Male et al., "Advanced Immunology", J.P. Lipincott Co., Chs. 6–10 (1987).

Wolfel et al (1989) J. Exp. Med 170: 797–810 "Lysis of human melanoma cells by autologous cytolytic T cell clones".

Kwon et al (1987) PNAS 84: 7473–7477 "Isolation and sequence of a cDNA clone for human tyrosinase that maps at the mouse c–albino locus".

*Primary Examiner*—Charles L. Patterson, Jr.
*Assistant Examiner*—Tekchand Saidha
*Attorney, Agent, or Firm*—Felfe & Lynch

[57] ABSTRACT

The invention relates to nucleic acid molecules coding for a tumor rejection antigen precursor. Specifically, the tumor rejection antigen precursor, or "TRAP", is processed into at least one tumor rejection antigen, which is presented by HLA-A2 molecules. Ramifications of the discovery are also set forth.

2 Claims, 5 Drawing Sheets

FIG. 4

| NORMAL TISSUES | As |
|---|---|
| melanocytes SK | + |
| heart | − |
| liver | − |
| kidney BA4 | − |
| prostate Clontech | − |
| adrenals | − |
| adrenals | − |
| adrenals | − |
| adrenals pool Clontech | − |
| testis Clontech | − |
| testis LB451 | − |
| brain Clontech | − |
| fetal brain Clontech | − |
| lung LB175 | − |
| lung LB195 | − |
| skin LB 177 | − |
| CTL SK29 IVS B | − |

MELANOMA

| CELL LINES | | TUMOR SAMPLES | |
|---|---|---|---|
| LB24-MEL | + | LB239-MEL | + |
| SK23-MEL | + | LB15-MEL | + |
| LE518-MEL | + | LB492-MEL | + |
| LB38-MEL | + | LB503-MEL | + |
| MZ13-MEL | − | LB435-MEL | + |
| LB33-MEL | − | LB224-MEL | + |
| LB3-MEL | + | LG18-MEL | + |

| OTHER TUMOR CELL LINES | |
|---|---|
| LB23 sarcoma | − |
| LE89.15 kidney tumor | − |
| BT20 breast carcinoma | − |
| LB63 colon carcinoma | − |
| T cell leukemia | − |

5,854,203

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 354 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
ATG  CGA  AGA  GAA  GAT  GCT  CAC  TTC  ATC  TAT  GGT  TAC  CCC  AAG  AAG  GGG        48
Met  Pro  Arg  Glu  Asp  Ala  His  Phe  Ile  Tyr  Gly  Tyr  Pro  Lys  Lys  Gly
                         5                          10                      15

GAC  GGC  CAC  TCT  TAC  ACC  ACG  GCT  GAA  GAG  GCC  GCT  GGG  ATC  GGC  ATC        96
His  Gly  His  Ser  Tyr  Thr  Thr  Ala  Glu  Glu  Ala  Ala  Gly  Ile  Gly  Ile
                    20                       25                       30

CTG  ACA  GTG  ATC  CTG  GGA  GTC  TTA  CTG  CTC  ATC  GGC  TGT  TGG  TAT  TGT       144
Leu  Thr  Val  Ile  Leu  Gly  Val  Leu  Leu  leu  Ile  Gly  Cys  Trp  Tyr  Cys
               35                       40                       45

AGA  AGA  CGA  AAT  GGA  TAC  AGA  GCC  TTG  ATG  GAT  AAA  AGT  CTT  CAT  GTT       192
Arg  Arg  Arg  Asn  Gly  Tyr  Arg  Ala  Leu  Met  Asp  Lys  Ser  Leu  His  Val
          50                       55                       60
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| GGC | ACT | CAA | TGT | GCC | TTA | ACA | AGA | AGA | TGC | CCA | CAA | GAA | GGG | TTT | GAT | 240 |
| Gly | Thr | Gln | Cys | Ala | Leu | Thr | Arg | Arg | Cys | Pro | Gln | Glu | Gly | Phe | Asp |     |
| 65  |     |     |     |     | 70  |     |     |     | 75  |     |     |     |     |     | 80  |     |
| CAT | CGG | GAC | AGC | AAA | GTG | TCT | CTT | CAA | GAG | AAA | AAC | TGT | GAA | CCT | GTG | 288 |
| His | Arg | Asp | Ser | Lys | Val | Ser | Leu | Gln | Glu | Lys | Asn | Cys | Glu | Pro | Val |     |
|     |     |     |     | 85  |     |     |     |     | 90  |     |     |     |     | 95  |     |     |
| GTT | CCC | AAT | GCT | CCA | CCT | GCT | TAT | GAG | AAA | CTC | TCT | GCA | GAA | CAG | TCA | 336 |
| Val | Pro | Asn | Ala | Pro | Pro | Ala | Tyr | Glu | Lys | Leu | Ser | Ala | Glu | Gln | Ser |     |
|     |     |     | 100 |     |     |     |     | 105 |     |     |     | 110 |     |     |     |     |
| CCA | CCA | CCT | TAT | TCA | CCT |     |     |     |     |     |     |     |     |     |     | 354 |
| Pro | Pro | Pro | Tyr | Ser | Pro |     |     |     |     |     |     |     |     |     |     |     |
|     |     | 115 |     |     |     |     |     |     |     |     |     |     |     |     |     |     |

( 2 ) INFORMATION FOR SEQ ID NO: 2:

( i ) SEQUENCE CHARACTERISTICS:
        ( A ) LENGTH: 676 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

| | | | | | | |
|---|---|---|---|---|---|---|
| TCTTCATACA | CGCGGCCAGC | CAGCAGACAG | AGGACTCTCA | TTAAGGAAGG | TGTCCTGTGC | 60 |
| CCTGACCCTA | CAAGATGCCA | AGAGAAGATG | CTCACTTCAT | CTATGGTTAC | CCCAAGAAGG | 120 |
| GGCACGGCCA | CTCTTACACC | ACGGCTGAAC | AGGCCGCTGG | GATCGGCATC | CTGACAGTGA | 180 |
| TCCTGGGAGT | CTTACTGCTC | ATCGGCTGTT | GGTATTGTAG | AAGACGAAAT | GGATACAGAG | 240 |
| CCTTGATGGA | TAAAAGTCTT | CATGTTGGCA | CTCAATGTGC | CTTAACAAGA | AGATGCCAC  | 300 |
| AAGAAGGGTT | TGATCATCGG | GACAGCAAAG | TGTCTCTTCA | AGAGAAAAAC | TGTGAACCTG | 360 |
| TGGTTCCCAA | TGCTGCAGGT | GCTTATGAGA | AACTCTCTGC | AGAACAGTCA | GGACCACCTT | 420 |
| ATTCACCTTA | AGAGCCAGCG | AGACACCTGA | GACATGGCTG | AAATTATTTC | TCTCACACTT | 480 |
| TTGCTTGAAT | TTAATACAGA | CATCTAATGT | TCTCCTTTGG | AATCCTGTAG | GAAAAATGCA | 540 |
| AGCCATCTCT | AATAATAAGT | CAGTGTTAAA | ATTTTAGTAG | GTCCGCTAGC | AGTACTAATC | 600 |
| ATGTGAGGAA | ATGATGAGAA | ATATTAAATT | GGGAAAACTC | CATCAATAAA | TGTTGCAAAT | 660 |
| GCATAGTAAA | AAAAAA | | | | | 676 |

TUMOR REJECTION ANTIGEN PRECURSOR PROCESSED TO AT LEAST ONE TUMOR REJECTION ANTIGEN PRESENTED BY HLA-A2

This application is a Divisional of U.S. patent application Ser. No. 08/032,978 filed Mar. 18, 1993, and now U.S. Pat. No. 5,620,886.

FIELD OF THE INVENTION

This invention relates to a nucleic acid molecule which codes for a tumor rejection antigen precursor. More particularly, the invention concerns a gene, whose tumor rejection antigen precursor is processed, inter alia, into at least one tumor rejection antigen that is presented by HLA-A2 molecules on cell surfaces.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., Advanced Immunology (J.P. Lipincott Company, 1987), especially chapters 6–10. The interaction of T cell and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Recently, much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLS. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes.

In U.S. patent application Ser. No. 938,334, the disclosure of which is incorporated by reference, nonapeptides are taught which are presented by the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993 and incorporated by reference, the fact that the MAGE-1 expression product is processed to a second TRA is disclosed. This second TRA is presented by HLA-C10-molecules. The disclosure shows that a given TRAP can yield a plurality of TRAs.

In U.S. patent application Ser. No. 994,928, filed Dec. 22, 1992, and incorporated by reference herein, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

It has now been found that another nucleic acid molecule codes for a tumor rejection antigen precursor which differs from those described previously. The TRAP of the invention is processed to at least one tumor rejection antigen that is presented by HLA-A2 molecules; however sequence analysis indicates that the TRAP of the invention is not, nor is it related to, tyrosinase. Thus the invention relates to a nucleic acid molecule which codes for a tumor rejection antigen precursor, or "TRAP" molecule. This "TRAP" molecule is not tyrosinase. Further, the TRAP of the invention is processed to at least one tumor rejection antigen, or "TRA", which is presented by HLA-A2 molecules. The TRA is not tyrosinase related, and other TRAs derived from the TRAPs of the invention may be presented by other HLA molecules.

The invention and various aspects thereof will be elaborated upon in the disclosure which follows.

BRIEF DESCRIPTION OF THE FIGURES

FIG. 4 presents a panel of tissues, cell lines and tumors tested for expression of the gene AaG1cl24 using polymerase chain reaction (PCR) using oligonucleotide probes derived from the nucleic acid molecule described herein.

DETAILED DESCRIPTION OF PREFERRED EMBODIMENTS

Example 1

A melanoma cell line, "LB-39-MEL" was established from melanoma cells taken from patient LB39, using standard methodologies. Once the cell line was established, a sample thereof was irradiated, so as to render it non-proliferative. These irradiated cells were then used to isolate cytolytic T cells ("CTLs") specific thereto.

A sample of peripheral blood mononuclear cells ("PBMCs") was taken from patient LB39, and contacted to the irradiated melanoma cells. The mixture was observed for lysis of the melanoma cells, which indicated that CTLs specific for a complex of peptide and HLA molecule presented by the melanoma cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS, and incubated for 45 minutes at 37° C. with 200 $\mu$Ci/ml of Na($^{51}$Cr)O$_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. Samples of PBLs were added in 100 ul of the same medium, and assays were carried out in duplicate. Plates were centrifuged for 4 minutes at 100 g, and incubated for four hours at 37° C. in at 80% of $CO_2$ atmosphere.

Plates were centrifuged again, and 100 ul aliquots of supernatant were collected and counted. Percentage of $^{51}$Cr release was calculated as follows:

$$\% \,^{51}Cr \text{ release} = \frac{(ER - SR)}{(MR - SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL Activity were expanded and cloned via limiting dilution, and were screened again, using the same methodology. The CTL clone LB39-CTL I/95 was thus isolated.

Figure 1A:
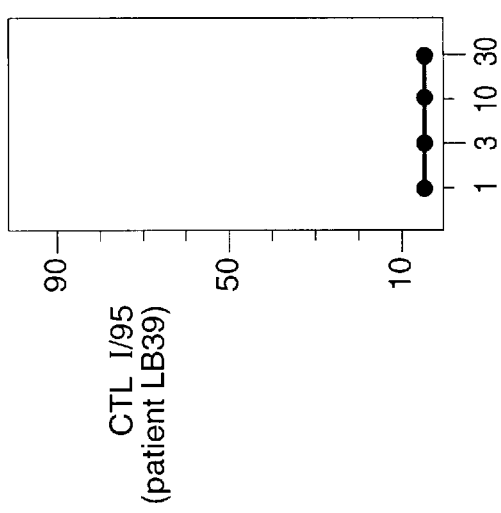
FIGS. 1A–1C present results of cell lysis experiments using CTL clone I/95 against LB39-MEL, K562, and LB39 blasts.
Figure 1B:
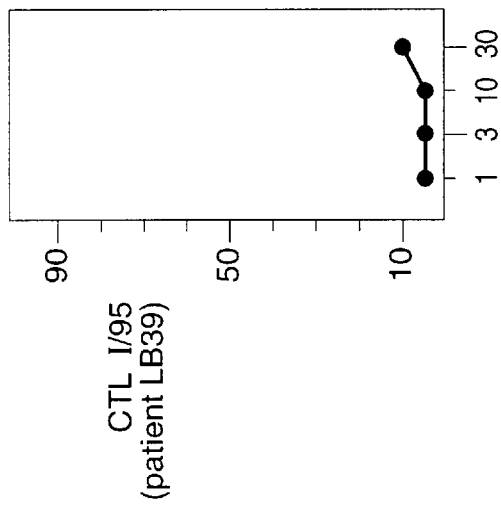
Figure 1C:
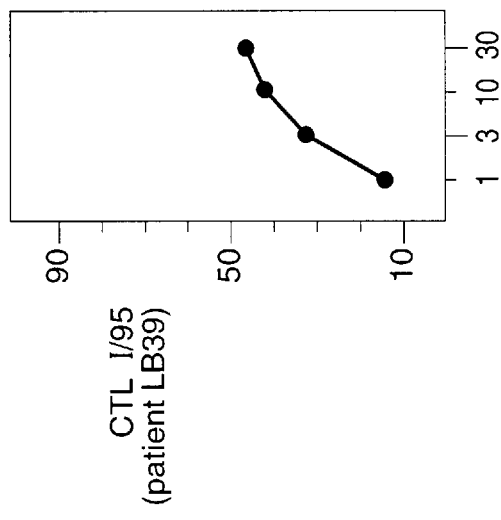
Figure 1D:
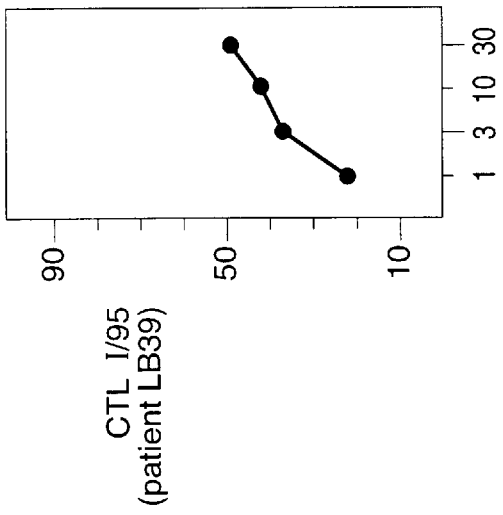
FIGS. 1D–1E show lysis using CTL clone I/95 against SK23-MEL and SK29-MEL.
Figure 1E:
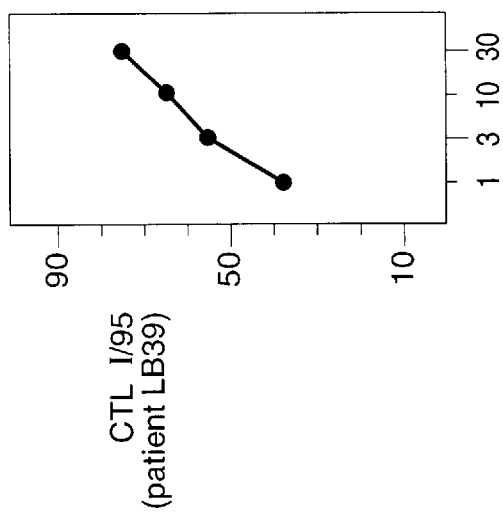

The same method was used to test target K562 cells, as well as autologous, PHA induced T cell blasts. These results, presented in FIG. 1A, show that this CTL clone recognizes and lyses the melanoma cell line, but neither of K562 or the T cell blasts. The CTL, LB39-CTL I/95, was then tested against melanoma cell lines SK23-MEL and SK29 MEL, in the same manner described supra. Cells from both of these lines were also lysed. These lines were both isolated from patients who were typed as HLA-A2, as was LB39. This suggested that the CTL clone LB39-CTL I/95 recognized an antigen presented by HLA-A2.

Example 2

Further studies were carried out to determine if LB39-CTL I/95 also produced tumor necrosis factor ("TNF") when contacted with target cells. The method used was that described by Traversari et al., Immunogenetics 35: 145–152 (1992), the disclosure of which is incorporated by reference. Briefly, samples of the CTL line were combined with samples of a target cell of interest, in culture medium. After 24 hours, supernatant from the cultures was removed, and then tested on TNF sensitive WEHI cells. In addition to LB39-MEL and SK23-MEL, described supra, another HLA-A2 line, i.e., SK29-MEL.1, an HLA-A2 loss variant, i.e., SEK29-MEL1.22, and a non HLA-A2 line, i.e., MZ2-MEL, which is HLA-A1, were tested.

Figure 2:
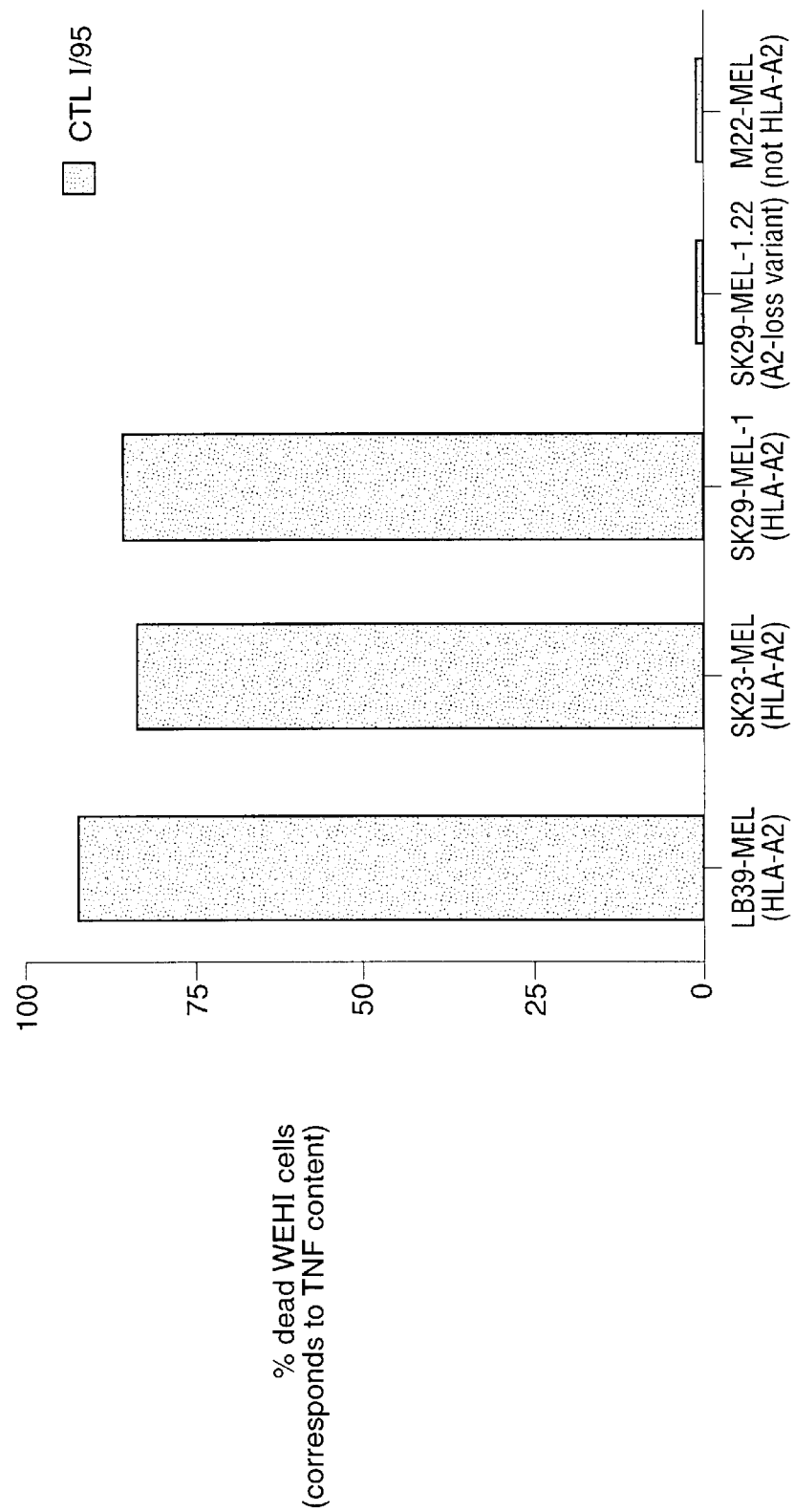
FIG. 2 sets forth results of a TNF release assay using various cell lines with CTL I/95.

The results, presented in terms of the percentage of WEHI cells which died upon exposure to the supernatant, are shown in FIG. 2. These results show that the HLA-A2 loss variant SK 29-MEL.1.22 is no longer capable of stimulating the CTL clone, thus confirming that the antigen recognized by LB39-CTL-I/95 is presented by HLA-A2.

Example 3

The results from Example 2 indicated that SK MEL 29.1 presented the target antigen of interest. As such, it was used as a source of total mRNA to prepare a cDNA library.

Total RNA was isolated from the cell line. The mRNA was isolated using an oligo-dT binding kit, following well recognized techniques. Once the mRNA was secured, it was transcribed into cDNA, again using standard methodologies. The cDNA was then ligated to EcoRI adaptors and cloned into the EcoRI site of plasmid pcDNA-I/Amp, in accordance with manufacturer's instructions. The recombinant plasmids were then electroporated into JM101 $E.$ $coli$ (electroporation conditions: 1 pulse at 25 $\mu$farads, 2500 V).

The transfected bacteria were selected with ampicillin (50 $\mu$g/ml), and then divided into 800 pools of 100 clones each. Each pool represented about 50 different cDNAs, as analysis showed that about 50% of plasmids contained an insert. Each pool was amplified to saturation, and plasmid DNA was isolated via alkaline lysis, potassium acetate precipitation without phenol extraction, following Maniatis et al., in Molecular Cloning: A Laboratory Manual (Cold Spring Harbor, N.Y., 1982).

Example 4

Following preparation of the library described in Example 3, the cDNA was transfected into eukaryotic cells. The transfections, described herein, were carried out in duplicate. Samples of COS-7 cells were seeded, at 15,000 cells/ well into tissue culture flat bottom microwells, in Dulbeco's modified Eagles Medium ("DMEM") supplemented with 10% fetal calf serum. The cells were incubated overnight at 37° C., medium was removed and then replaced by 30 $\mu$l/well of DMEM medium containing 10% Nu serum, 400 $\mu$g/ml DEAE-dextran, 100 $\mu$M chloroquine, 100 ng of plasmid pcDNA-I/Amp-A2 and 100 ng of DNA of a pool of the CDNA library described supra. Plasmid pcDNA-I/Amp-A2 contains the HLA-A2 gene from SK29-MEL. Following four hours of incubation at 37° C., the medium was removed, and replaced by 50 $\mu$l of PBS containing 10% DMSO. This medium was removed after two minutes and replaced by 200 $\mu$l of DMEM supplemented with 10% of FCS.

Following this change in medium, COS cells were incubated for 48 hours at 37° C. Medium was then discarded, and 1000 cells of CTL I/95 were added, in 100 $\mu$l of Iscove medium containing 10% pooled human serum, supplemented with 25 U/ml of IL-2. Supernatant was removed after 24 hours, and TNF content was determined in the assay on WEHI cells, as described by Traversari et al., supra, previously incorporated by reference.

Of the 800 pools tested, 99% stimulated TNF release, to a concentration of from 3–6 pg/ml in the supernatant. Two pools gave yields over 8 pg/ml, with a duplicate well also yielding over 8 pg/ml.

Example 5

Figure 3A:
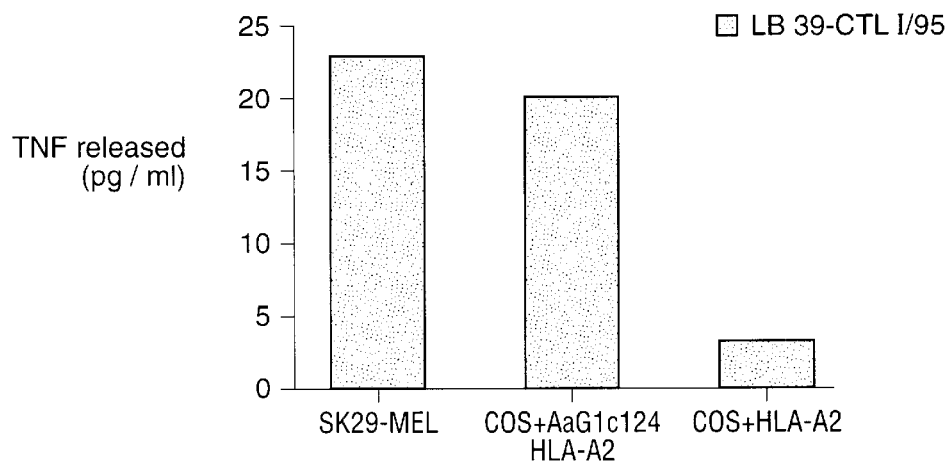
FIG. 3A shows TNF release induced by different cell lines, including transfectants, when tested with CTL clone I/95.

The two pools showing high yields of TNF in the supernatant were selected for further study. Specifically, the bacteria were cloned, and 800 bacteria were tested from each pool. Plasmid DNA was extracted therefrom, transfected into a new sample of COS cells in the same manner as described supra, and the cells were again tested for stimulation of LB39-CTL clone I/95. One positive clone was found, referred to as AaG1cl24. Convincing evidence that the transfected cells were recognized by CTLs was obtained by carrying out a comparative test of COS cells transfected with cDNA from the positive clone and the HLA-A2 gene, COS cells transfected only with HLA-A2, and line SK29-MEL. TNF release in CTL supernatant was measured by testing it on WEHI cells, as referred to supra. The optical density of the surviving WEHI cells was measured using MTT. FIG. 3A shows the results obtained with CTL clone I/95.

Figure 3B:
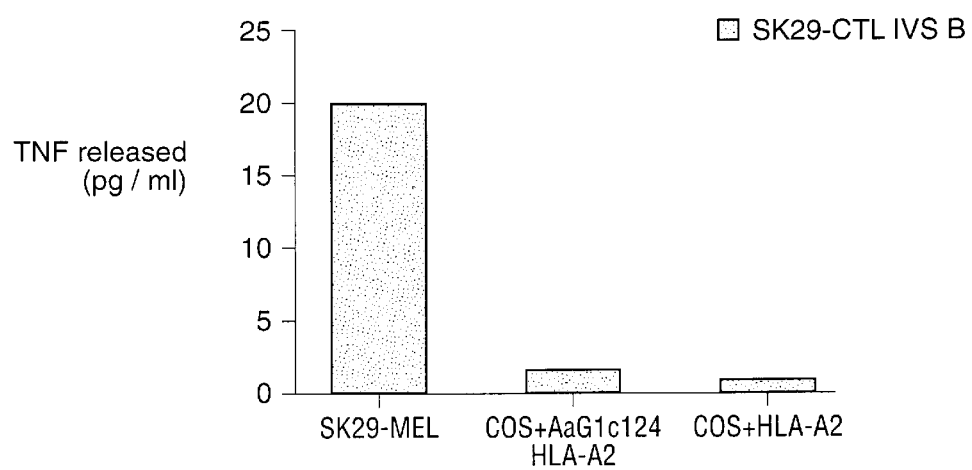
FIG. 3B presents TNF release data using CTL clone IVSB.

Further tests showed that the peptide presented by HLA-A2 in the transfected cells was different from that observed previously, i.e., a tyrosinase derived peptide. CTL clone IVSB is specific to complexes of tyrosinase derived peptide and HLA-A2. When this CTL clone was contacted to cells transfected with AaG1cl24 and HLA-A2, TNF release was minimal, as shown in FIG. 3B.

Example 6

The cDNA from the positive clone was removed, and sequenced following art known techniques. A sequence search revealed that the plasmid insert showed no homology to known genes or proteins. SEQUENCE ID NO: 1 presents cDNA nucleotide information, showing a large, open reading frame from positions 75 to 431, corresponding to a protein product of 119 amino acids. Sequence ID NO: 2 sets forth the extended sequence of which SEQ ID NO: 1 is a part.

Example 7

Figure 3C:
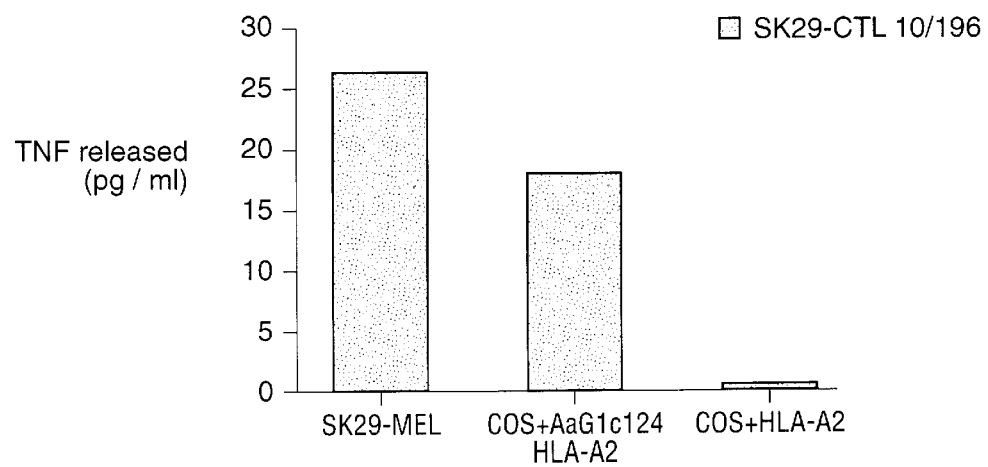
FIG. 3C shows TNF release using CTL clone 10/196.

In the same manner that CTL clone LB39-CTL I/95 was isolated, a sample of PBMCs and a melanoma cell line developed from patient SK29(AV) were used to isolate CTL clone SK29-CTL 10/196. This new cell line was tested in the same manner as is set forth in Example 5. The results of the assays, depicted in FIG. 3C, show that the tumor rejection antigen coded for by AaG1cl24 (referred to as antigen "LB39-Aa" hereafter), is also recognized by this CTL clone. These experiments indicate that other patients can, and in fact do, generate CTLs specific for this antigen.

Oligonucleotide probes were derived from the described sequences, and were used in standard polymerase chain reaction methodologies to determine expression of the gene in normal tissues, tumors, and tumor cell lines. These results are presented in FIG. 4, and show that among normal tissues tested, only melanocytes expressed the gene. Note the expression in all tumor samples and/or melanoma cell lines tested.

The foregoing experiments describe a newly isolated nucleic acid sequence coding for a tumor rejection antigen precursor, a "TRAP" molecule. The molecule is processed intracellularly in a manner which leads to production of at least one tumor rejection antigen, or "TRA", which is presented by HLA-A2 molecules. While it has been observed previously that HLA-A2 molecules present peptides derived from tyrosinase, the nucleic acid sequences of the invention do not code for tyrosinase, and the TRAs are not tyrosinase derived.

The invention thus involves an isolated nucleic acid molecule which codes for a tumor rejection antigen precursor, or "TRAP", with the proviso that the TRAP is not tyrosinase. The TRAP coded for is one which is processed to at least one tumor rejection antigen, or TRA, which is presented by HLA-A2 molecules on cell surfaces. The nucleic acid molecules of the invention may be, e.g., genomic DNA, ("gDNA"), complementary DNA ("cDNA"), or a form of RNA. The invention also involves isolated nucleic acid molecules which are complementary to the molecules described above. An especially preferred form of the invention is a molecule which contains the sequence set forth in SEQ ID NO: 1.

Also encompassed by the invention are vectors which contain the nucleic acid molecules of the invention, operably linked to a promoter. The vectors may also include a molecule coding for HLA-A2. As these two molecules, i.e., HLA-A2 and the TRAP are necessary to generate a cytolytic T cell response, the invention also encompasses expression systems where nucleic acid molecules coding for TRAP and for HLA-A2 are presented as separate portions in, e.g., a kit. The invention also encompasses cell lines transfected by the vectors described herein, be these prokaryotic cells, such as E. coli, or eukaryotic cells, such as Chinese hamster ovary ("CHO") or COS cells.

As indicated, the complexes of TRA and HLA-A2 provoke a cytolytic T cell response, and as such isolated complexes of the tumor rejection antigen and an HLA-A2 molecule are also encompassed by the invention, as are isolated tumor rejection antigen precursors coded for by the previously described nucleic acid sequences.

The invention as described herein has a number of uses, some of which are described herein. First, the identification of a tumor rejection antigen which is specifically presented by HLA-A2 molecules, as well as a nucleic acid molecule coding for its parallel tumor rejection antigen precursor permits the artisan to diagnose a disorder characterized by expression of the TRAP. These methods involve determining expression of the TRAP gene, and/or TRAs derived therefrom, such as TRA presented by HLA-A2. Other TRAs may also be derived from the TRAPs of the invention and presented by different HLA molecules. In the former situation, such determinations can be carried out via any standard nucleic acid determination assay, including the polymerase chain reaction, or assaying with labelled hybridization probes. In the latter situation, assaying with binding partners for complexes of TRA and HLA, such as antibodies, is especially preferred.

The isolation of the TRAP gene also makes it possible to isolate the TRAP molecule itself, especially TRAP molecules containing the amino acid sequence of SEQ ID NO: 1. These isolated molecules when presented as the TRA, or as complexes of TRA and HLA, such as HLA-A2, may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to prove a CTL response, or be cells which express both molecules without transfection. Further, the TRAP molecule, its associated TRAs, as well as complexes of TRA and HLA, may be used to produce antibodies, using standard techniques well known to the art.

When "disorder" is used herein, it refers to any pathological condition where the tumor rejection antigen precursor is expressed. An example of such a disorder is cancer melanoma in particular.

Therapeutic approaches based upon the disclosure are premised on a response by a subject's immune system, leading to lysis of TRA presenting cells, such as HLA-A2 cells. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein are widely available, as are other suitable host cells.

To detail the therapeutic methodology, referred to as adoptive transfer (Greenberg, J. Immunol. 136(5): 1917 (1986); Reddel et al., Science 257: 238 (Jul. 10, 1992); Lynch et al., Eur. J. Immunol. 21: 1403–1410 (1991); Kast et al., Cell 59: 603–614 (No. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the HLA/TRA complex. This can be determined very easily, as the art is very familiar with methods for identifying cells which present a particular HLA molecule, as well as how to identify cells expressing DNA containing the indicated sequences. Once isolated, such cells can be used with a sample of a subject's abnormal cells to determine lysis in vitro. If lysis is observed, then the use of specific CTLs in such a therapy may alleviate the condition associated with the abnormal cells. A less involved methodology examines the abnormal cells for HLA phenotyping, using standard assays, and determines expression via amplification using, e.g., PCR.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining the tumor rejection antigen or the precursor itself with an adjuvant to facilitate incorporation into HLA-A2 presenting cells which present the HLA molecule of interest. The TRAP is processed to yield the peptide partner of the HLA molecule while the TRA is presented without the need for further processing.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated tumor rejection antigen precursor molecule which is not a tyrosinase, and which comprises an amino acid sequence corresponding to a peptide which forms a complex with HLA-A2 molecule, said isolated tumor rejection antigen precursor molecule having an amino acid sequence encoded by the nucleotide sequence set forth in SEQ ID NO: 1.

2. Composition of matter comprising the isolated tumor rejection antigen precursor of claim 1, and an adjuvant.

* * * * *